US00PP15191P2

(12) United States Plant Patent
Olesen et al.

(10) Patent No.: US PP15,191 P2
(45) Date of Patent: Sep. 28, 2004

(54) MINIATURE ROSE PLANT 'POULRA023'

(50) Latin Name: *Rosa hybrid*
Varietal Denomination: POULra023

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,161

(22) Filed: Dec. 16, 2003

(51) Int. Cl.[7] ..... A01H 5/00
(52) U.S. Cl. ..... Plt./117
(58) Field of Search ..... Plt./117

*Primary Examiner*—Kent Bell
*Assistant Examiner*—S B McCormick-Ewoldt

(57) ABSTRACT

A new miniature rose which has abundant, white flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrid.*
Variety denomination: 'POULra023'.

SUMMARY OF THE INVENTION

The present invention constitutes a new and distinct variety of miniature rose plant which originated from a controlled crossing between the female seed parent, an unnamed plant, and the pollen parent, 'KORstoffein', described and illustrated in U.S. Plant Pat. No. 11,242 dated Feb. 22, 2000. The two parents were crossed and the resulting seeds were planted in a controlled environment. The new variety is named 'POULRa023'.

The new rose may be distinguished from its pollen parent, 'KORstoffein', by the following combination of characteristics:

1. The pollen parent has 25 to 30 petals, while 'POULra023' has an average of 16 petals.
2. 'KORstoffein' has a petal color of Yellow-Orange Group 19D while the same of 'POULra023' is White Group 155D.

The new variety may be distinguished from its seed parent, by the following combination of characteristics:

1. The seed parent has a Red flower color, while 'POULra023' has a white flower color.
2. Flowers of the seed parent have more flower petals than 'POULra023'.

The objective of the hybridization of this rose variety for commercial culture was to create a new and distinct variety with unique qualities, such as:

1. Uniform and abundant white flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra023' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULra023' was selected by the inventors as a single plant from the progeny of the hybridization in 2000.

Asexual reproduction of 'POULra023' by cuttings and traditional budding was first done by L. Pernille and Mogens N. Olesen in their nursery in Fredensborg, Denmark in 2001. This initial and other subsequent propagations conducted in controlled environments have demonstrated that the characteristics of 'POULra023' are true to type and are transmitted from one greenhouse to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra023'. Specifically illustrated in the drawing:

FIG. 1.1; Open flower, stem showing the attachment of leaves and peduncles;

FIG. 1.2; Flower buds at various stages of development;

FIG. 1.3; Sepals, receptacle, and pedicel;

FIG. 1.4; Mature and juvenile leaves;

FIG. 1.5; Flower petals, detached

FIG. 1.6; Bare stem exhibiting thorns.

DETAILED DESCRIPTION OF THE VARIETY

The following is a description of 'POULra023', as observed in its growth in glasshouses in Fredensborg, Denmark. Observed plants were cultivated in 10 cm pots, for a period of 3 months. Color references are made using The Royal Horticultural Society (London, England) Colour Chart, 1995, except where common terms of color are used.

For a comparison, several physical characteristics of the rose variety 'POULra015', a rose variety from the same inventors described and illustrated in U.S. Plant Pat. No. 14,309 are compared to 'POULra023' in Chart 1.

CHART 1

| | 'POULra023' | 'POULra015' |
|---|---|---|
| General tonality | White Group 155D with intonations of Orange-White Group 159C | Yellow Group 11D |
| Petal count | 16 | 13 to 15 |
| Flower diameter | 46 mm. | 55 mm. |

FLOWER AND FLOWER BUD

Blooming habit: Continuous.

Flower bud:

*Size.*—Upon opening, 19 mm in length from base of receptacle to end of bud. Diameter of flower bud 11 mm.

*Bud form.*—Pointed ovoid.

*Bud color.*—As sepals unfold, White Group 155D to Orange-White Group 159D.

*Sepals.*—Upper surface: Texture: Moderately pubescent. Color: Yellow-Green Group 147A. Anthocyanin: Greyed-Orange Group 166A at the apex. Lower surface: Color: Yellow-Green Group 147A. Anthocyanin: Greyed-Orange Group 166A at the apex. Shape: Sepal apex is cirrose. Base is flat at union with peduncle. Sepal margin: Margins have strong foliaceous appendages on three of the five sepals. Stipitate glands are present in medium quantity. Size: 26 mm (l)×15 mm (w).

*Receptacle.*—Surface: Smooth. Shape: Urn-Shaped. Size: 5 mm (h)×7 mm (w). Color: Yellow-Green Group 144B.

*Peduncle.*—Surface: Smooth with stipitate glands in medium quantity. Length: 20 to 25 mm in length. Color: Yellow-Green Group 144B. Strength: Strong. Diameter: 4 mm.

*Borne.*—Singularly.

Flower bloom:

*Fragrance.*—Light floral scent.

*Duration.*—The blooms have a duration on the plant of approximately 15 to 18 days. Afterwards, petals fall cleanly away from plant.

*Size.*—For an 8–11 cm pot rose, average flower diameter is 46 mm when open. Average flower depth is 16 mm when open.

*Form.*—High centered open cup. Shape of flower when viewed from the side: Upon opening, upper part: Flat. Upon opening, lower part: Convex. Open flower, upper part: Flattened convex. Open flower, lower part: Concave.

*Petalage.*—16 petals under normal conditions with an average of 3 petaloids.

Color:

*Upon opening, petals.*—Outermost petals: Outer side: White Group 155D with intonations of Orange-White Group 159C. Inner side: White Group 155D to Green-White Group 157D. Innermost petals: Outer side: White Group 155D with very light intonations of Red Group 38D. Inner side: White Group 155D to Green-White Group 157D.

*Upon opening, basal petal spots.*—No distinctive coloration at petal base observed.

*After opening, petals.*—Outermost petals: Outer side: White Group 155D with very light intonations of Red Group 38D. Inner side: Green-White Group 157A to 157D. Innermost petals: Outer side: White Group 155D with very light intonations of Red Group 38D. Inner side: Green-White Group 157A to 157D.

*After opening, basal petal spots.*—No distinctive coloration at petal base observed.

General tonality: On open flower White Group 155D with intonations of Orange-White Group 159C. No change in the general tonality at the end of the 10th day.

Petals:

*Petal reflex.*—Somewhat.

*Petal edge.*—Entire.

*Shape.*—Apex: Round. Base: Rounded.

*Size.*—20 to 24 mm (l)×22 to 25 mm (w).

*Texture.*—Smooth.

*Thickness.*—Thick.

*Petaloids.*—Quantity: 3 on average. Size: 6 mm (l)×3 mm (w). Color: White Group 155D. Shape: Elliptical.

Reproductive organs:

*Pistils.*—Length: 5 mm long. Quantity: 29 (actual count).

*Pollen.*—Color: None observed.

*Anthers.*—Size: 2 mm long. Color: Greyed-Yellow Group 162B. Quantity: 56 (actual count).

*Filaments.*—Color: Yellow Group 4C. Length: 4 mm to 6 mm.

*Stigmas.*—Level with anthers. Color: Red-Purple Group 65A to 65B.

*Styles.*—Color: Yellow-Green Group 149D.

*Seed formation.*—No hips observed.

PLANT

Plant growth: The average height of the plant is 17 cm and the average width is 10 cm.

Stems:

*Color.*—Young wood: Yellow-Green Group 144A. Older wood: Yellow-Green Group 146B.

*Stem size.*—Average length is 15 cm from flower to first branch. Stem diameter is 2 mm.

*Thorns.*—Incidence: None.

*Surface.*—Young wood: Smooth. Older wood: Smooth.

*Internodal distance.*—15 mm.

Plant foliage: Normal number of leaflets on normal leaves in middle of the stem: 5 to 7 leaflets.

*Leaf size.*—Compound leaves are 60 mm (l)×42 mm (w).

*Quantity.*—6 leaves per 10 cm of stem.

*Color.*—Upper leaf surface: Green Group 146A. Lower leaf surface: Yellow-Green Group 147B to 147C. Juvenile foliage: Upper leaf surface: Yellow-Green Group 144A. Lower leaf surface: Green Group 138B. Anthocyanin intonation: Yes. Location: Margins and lower surface of leaflets. Color: Greyed-Orange Group 176A.

Plant leaves and leaflets:

*Stipules.*—Size: 7 mm in length. Color: Green Group 137A. Margins: Stipitate glands in medium quantity.

*Petiole.*—Length: 12 mm. Color: Yellow-Green Group 144A. Underneath: Yellow-Green Group 144A.

*Rachis.*—Length: 20 mm. Color: Yellow-Green Group 144A. Underneath: Yellow-Green Group 144A.

Anthocyanin: Greyed-Orange Group 176A. Other descriptive terms: Thorns present.

*Leaflet.*—Size: 35 mm (l)×20 mm (w). Edge: Serrated. Shape: Base shape is rounded. Apex shape is acute. Texture: Smooth. Surface: Matte. Thickness: Medium. Arrangement: Odd pinnate. Venation: Reticulate.

Disease resistance: Above average resistance to mildew, black spot, and Botrytis under normal growing conditions in Fredensborg, Denmark.

We claim:

1. A new and distinct variety of rose of the miniature class, substantially as herein illustrated and described as a distinct and novel rose plant variety due to its abundant, white flowers, vigorous growth, compact habit, suitability for production from softwood cuttings in pots, and durable flowers and foliage which make the variety suitable for distribution in the floral industry.

* * * * *

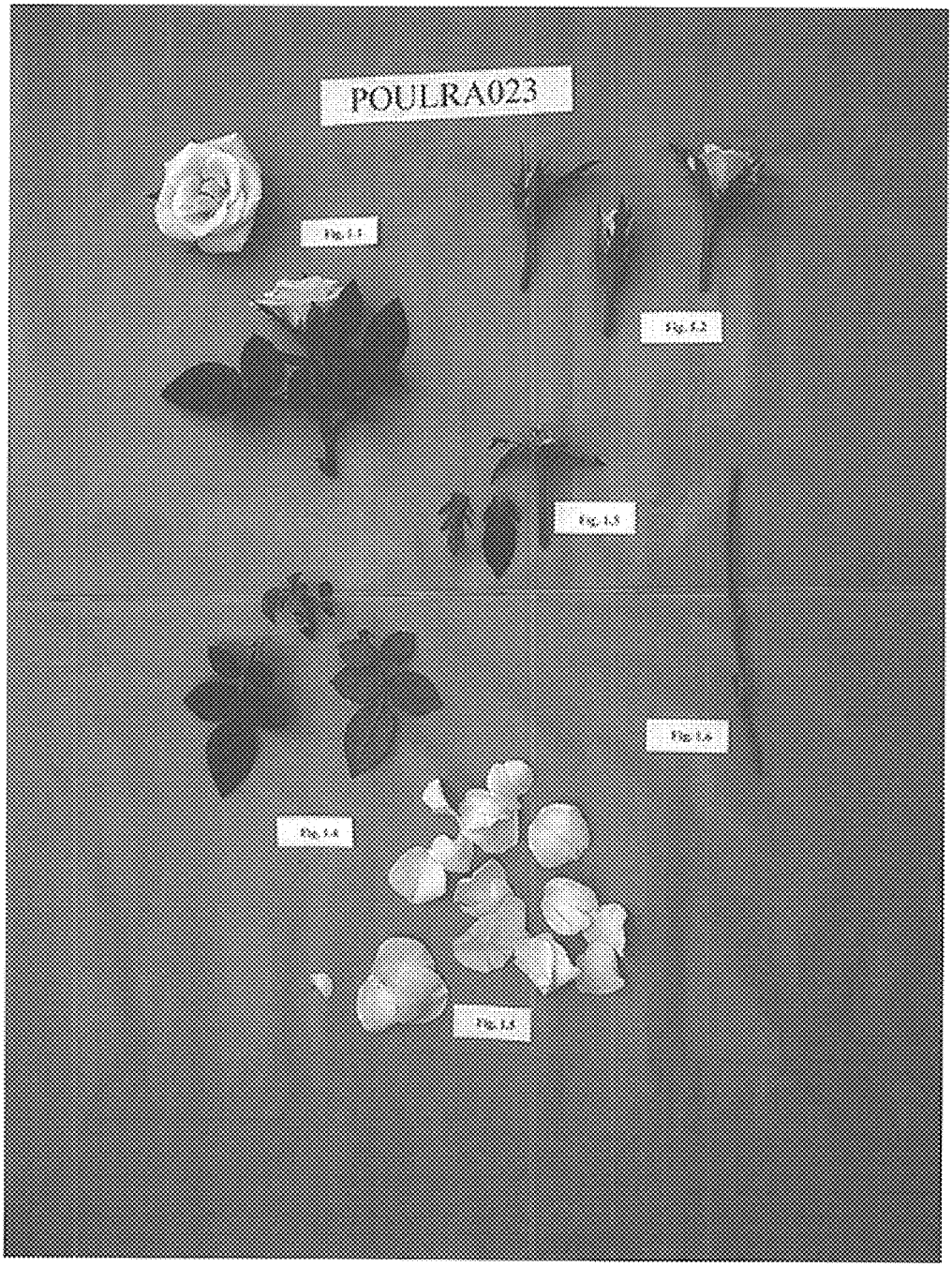
POULRA023